United States Patent
Inaba et al.

(10) Patent No.: US 8,986,938 B2
(45) Date of Patent: Mar. 24, 2015

(54) MICROBIAL ACTIVITY IMPROVEMENT AGENT, MICROBIAL ACTIVITY IMPROVEMENT METHOD, AND BIOLOGICAL WASTE TREATMENT METHOD

(75) Inventors: Hideki Inaba, Chigasaki (JP); Youhei Hashimoto, Yokosuka (JP); Nobuhiko Nomura, Tsukuba (JP); Masanori Toyofuku, Tsukuba (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 365 days.

(21) Appl. No.: 13/379,383

(22) PCT Filed: Jun. 22, 2010

(86) PCT No.: PCT/JP2010/060559
§ 371 (c)(1),
(2), (4) Date: Jan. 12, 2012

(87) PCT Pub. No.: WO2010/150784
PCT Pub. Date: Dec. 29, 2010

(65) Prior Publication Data
US 2012/0107914 A1 May 3, 2012

(30) Foreign Application Priority Data
Jun. 22, 2009 (JP) ................. 2009-147622

(51) Int. Cl.
| | |
|---|---|
| *G01N 33/53* | (2006.01) |
| *C12N 1/38* | (2006.01) |
| *C05F 17/00* | (2006.01) |
| *C02F 101/16* | (2006.01) |
| *C02F 101/34* | (2006.01) |
| *C02F 103/00* | (2006.01) |
| *C02F 103/06* | (2006.01) |
| *C02F 103/20* | (2006.01) |

(52) U.S. Cl.
CPC .............. *C12N 1/38* (2013.01); *C05F 17/0036* (2013.01); *C02F 2101/16* (2013.01); *C02F 2101/163* (2013.01); *C02F 2101/34* (2013.01); *C02F 2101/40* (2013.01); *C02F 2103/005* (2013.01); *C02F 2103/06* (2013.01); *C02F 2103/20* (2013.01); *C02F 2303/20* (2013.01); *C02F 2305/06* (2013.01)
USPC .............................................. 435/7.2; 435/29

(58) Field of Classification Search
USPC ....................................................... 435/7.2
See application file for complete search history.

(56) References Cited

U.S. PATENT DOCUMENTS

| | | |
|---|---|---|
| 6,001,868 A | 12/1999 | Firestone et al. |
| 2004/0063765 A1 | 4/2004 | Ammendola et al. |
| 2004/0251197 A1 | 12/2004 | Chandler |

FOREIGN PATENT DOCUMENTS

| | | |
|---|---|---|
| JP | 08-052486 | 2/1996 |
| JP | 2001-054379 A | 2/2001 |
| JP | 2004-276017 | 10/2004 |
| JP | 2005-505419 | 2/2005 |
| JP | 2005-517635 | 6/2005 |
| JP | 2006-102722 | 4/2006 |
| JP | 2008-101014 A | 5/2008 |
| JP | 2009-066505 | 4/2009 |
| WO | 2007/146831 A2 | 12/2007 |

OTHER PUBLICATIONS

Hwang et al. "Identification and quantification of sulfur and nitrogen containing odorous compounds in wastewater", Wat. Res., 1995, 29(2):711-718.*
International Search Report international application No. PCT/JP2010/060559 dated Jan. 17, 2012.
James H. Wynne and Wayne M. Stalick, "Synthesis of 3-[(1-Aryl)aminomethyl]indoles", J. Org. Chem. vol. 67, No. 16, Jan. 23, 2002, p. 5850-p. 5853.
Office Action mailed Feb. 12, 2014, issued in corresponding Japanese Patent Application No. 2011-519904.
Peter S. Sherin et al., "Experimental and Quantum Chemical Study of Photochemical Properties of 4-Hydroxyquinoline", Photochemical & Photobiological Sciences, vol. 8, No. 11, XP055047079, Jan. 1, 2009, 8 pages.
Stephen P. Diggle et al., "4-Quinolone Signalling in *Pseudomonas aeruginosa*: Old Molecules, New Perspectives", International Journal of Medical Microbiology, Urban and Fischer, DE, vol. 296, No. 2-3, XP028043326, Apr. 6, 2006, pp. 83-91.
European Search Report application No. 10792102.5-2104, dated Jan. 16, 2013.
International Search Report corresponding to International Application No. PCT/JP2010/060559 dated Jul. 27, 2010.

* cited by examiner

*Primary Examiner* — Bin Shen
(74) *Attorney, Agent, or Firm* — Squire Patton Boggs (US) LLP

(57) ABSTRACT

A compound selected from the group consisting of 4-quinolone and derivatives thereof, homoserine lactone derivatives, and indole and derivatives thereof, and salts thereof have an action of a microbial activity improvement agent, and when it is used for a microbial activity improvement method and a biological waste treatment method, the compound or the salt thereof is useful to achieve the improvement in the treatment capacity that transcends the limit of improvement in the treatment capacity of conventional biological waste treatment facilities.

4 Claims, 2 Drawing Sheets

MICROBIAL ACTIVITY IMPROVEMENT AGENT, MICROBIAL ACTIVITY IMPROVEMENT METHOD, AND BIOLOGICAL WASTE TREATMENT METHOD

CROSS REFERENCE TO RELATED APPLICATIONS

This application is a U.S. National Stage of International Application No. PCT/JP2010/060559 filed on Jun. 22, 2010, which claims priority from Japanese Application No. 2009-147622 filed on Jun. 22, 2009.

TECHNICAL FIELD

The present invention relates to a microbial activity improvement agent, a microbial activity improvement method, and a biological waste treatment method.

BACKGROUND ART

As a biological waste treatment technique to purify organic waste (pollutant) such as industrial wastewater, sewage, night soil, leachate, kitchen waste, and animal manure by a microbial degradation potential of organic compounds, an activated sludge method, methane fermentation, and the like are known. In these biological waste treatments, the ability of a biological waste treatment facility is higher as microbial activity involved with decomposition of wastes is higher and the abundance of microorganisms is higher.

As a method for maintaining a useful microorganism at a high concentration in a reaction tank of a biological waste treatment facility, techniques such as an adhesion carrier method, an entrapping carrier method, a self-granulated sludge method, a biological membrane filtration method, and a membrane bio-reactor are developed (e.g., see Patent Literatures 1 and 2). With the use of these methods, the biological waste treatment can be performed in more compact facilities.

As another method for increasing microbial concentration, a method in which a microorganism having especially high decomposition activity of a pollutant to be treated is isolated from soil and separately pure-cultured, and then the microorganism is added into a reaction tank is also developed.

Further, Patent Literature 3 discloses use of a specific compound for adjusting a microbial signaling system.

CITATION LIST

Patent Literature

Patent Literature 1: Japanese Patent Application Laid-Open Publication No. 8-52486
Patent Literature 2: Japanese Patent Application Laid-Open Publication No. 2009-66505
Patent Literature 3: National Publication of International Patent Application No. 2005-517635

SUMMARY OF INVENTION

Technical Problem

However, since the methods such as the adhesion carrier method, the entrapping carrier method, the self-granulated sludge method, the biological membrane filtration method, and the membrane bio-reactor have a limitation in the increase in microbial concentration within economic constraints, the amount of wastes that is treatable in biological waste treatment facilities is at most about 10 to 30 kg/m³/day in terms of chemical oxygen demand (COD) volume load.

Further, in the method in which a pure-cultured specific microorganism is added into a reaction tank, the microorganism thus added perishes by the natural selection in the reaction tank in most cases. In view of this, such an attempt that an isolated specific microorganism is formulated into a preparation thin), and is continuously added as appropriate so as to maintain the treatment capacity has been made, but its use application is limited due to economic constraints.

Although a method in which nutrients are added is conceivable as the method to improve the microbial activity, the addition of a sufficient amount of nutrients means that wastes should be added in large quantities, which impairs the meaning of biological waste treatment facilities and which does not work economically. Addition of minor components such as phosphorus, nitrogen, metal and the like may be carried out in some cases, but the addition does not significantly improve the microbial activity, although the addition provides a preventive effect on a reduction in the microbial activity.

In view of this, an object of the present invention is to achieve improvement in the treatment capacity of conventional biological waste treatment facilities that transcends the limits of improvement in the treatment capacity.

Solution to Problem

In one aspect, the present invention provides a microbial activity improvement agent including a compound selected from the group consisting of compounds represented by the following formulae (1) to (4) or a salt thereof:

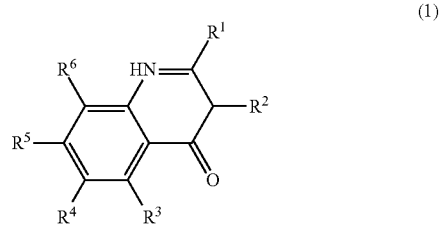

(1)

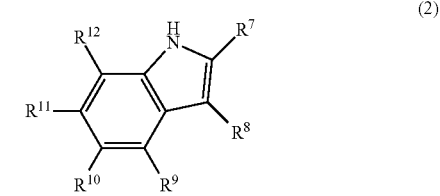

(2)

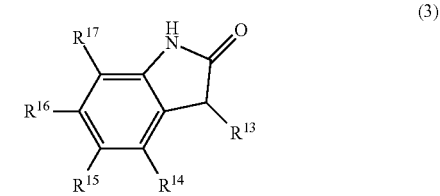

(3)

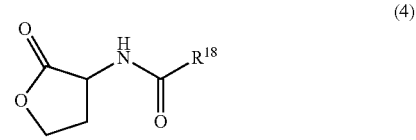

(4)

wherein $R^1$ to $R^6$ each independently represents a hydrogen atom, a hydroxyl group, or a $C_{1-6}$ alkyl group; $R^7$ to $R^{17}$ each independently represent a hydrogen atom or a group represented by any of the following formulae (5) to (7):

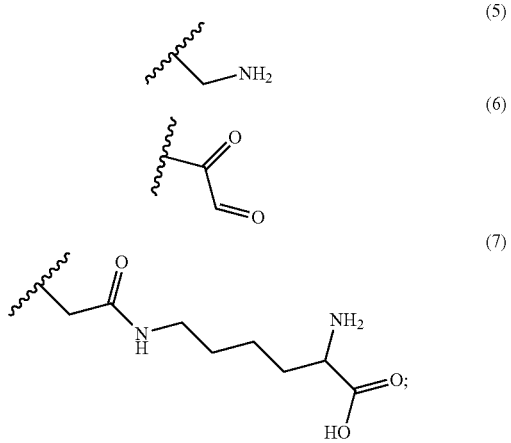

and $R^{18}$ represents a $C_{9-15}$ alkyl group optionally having an oxo group.

By adding an extremely small amount of the above microbial activity improvement agent into a reaction tank of a biological waste treatment facility, it is possible to improve the waste treatment capacity. This accordingly makes it possible to achieve, at a low cost, improvement in the treatment capacity of conventional biological waste treatment facilities that transcends the limit of improvement in the treatment capacity by a conventional method such as an adhesion carrier method, an entrapping carrier method, a self-granulated sludge method, a biological membrane filtration method, a membrane bio-reactor, a method in which a pure-cultured specific microorganism is added into a reaction tank, and a method in which nutrients are added.

It is more preferable that the microbial activity improvement agent include a compound selected from the group consisting of compounds represented by the following formulae (a) to (g) or a salt thereof:

(a) a compound represented by the above formula (1) wherein $R^1$ to $R^6$ are hydrogen atoms;

(b) a compound represented by the above formula (1) wherein $R^2$ to $R^6$ are hydrogen atoms, and $R^1$ is a methyl group;

(c) a compound represented by the above formula (1) wherein $R^1$ is a methyl group, $R^2$ is a hydroxyl group, and $R^3$ to $R^6$ are hydrogen atoms;

(d) a compound represented by the above formula (2) wherein $R^7$ to $R^{12}$ are hydrogen atoms;

(e) a compound represented by the above formula (2) wherein $R^7$ and $R^9$ to $R^{12}$ are hydrogen atoms, and $R^8$ is a group represented by any of the above formulae (5) to (7);

(f) a compound represented by the above formula (3) wherein $R^{13}$ to $R^{17}$ are hydrogen atoms; and (g) a compound represented by the above formula (4) wherein $R^{18}$ is a $C_{10-15}$ alkyl group or a 2-oxononyl group.

As described later, these compounds can be relatively easily prepared from sludge having a high treatment capacity of a target pollutant. Further, even at a biological waste treatment facility in which the treatment of pollutant has not worked anymore, by adding an extremely small amount of the compounds to its reaction tank, it is possible to recover the waste treatment capacity of the facility, and further to improve the waste treatment capacity. In other words, even under conditions where the waste treatment capacity decreases in general, it is possible to perform high-efficiency and stable waste treatment.

In another aspect, the present invention provides a microbial activity improvement method including the step of adding one or more of the microbial activity improvement agents described above into a cultural environment of a microorganism (into an environment where a microorganism exists). The environment where a microorganism exists means the following exemplary environments: a culture medium for culturing a microorganism; soil; organic waste such as industrial wastewater, sewage, night soil, leachate, kitchen waste, and animal manure; a reaction tank of a biological waste treatment facility; and an environment where the after-mentioned biofilm can be formed.

According to this method, it is possible to control, for example, formation of a microbial biofilm. The biofilm is a structure formed of a microorganism, and it is formed such that a microorganism attached to a substrate secretes a secretion called extracellular polysaccharides or EPS (Extracellar Polysaccaride S). For example, in medical treatment, Staphylococcus aureus or the like forms a biofilm in a catheter and a microorganism in the biofilm has high resistance to antibiotics and immunity, which may cause a problem in some cases.

By improving, for example, the metabolic activity of a microorganism involved with decomposition of a biofilm in an opportunistic infection, it is accordingly possible to obstruct the formation of a biofilm and to cause antibiotics to reach pathogenic bacteria.

This microbial activity improvement method is applicable to various targets, such as offshore structures and pipelines, which the biofilm formation affects. For example, the method can be applied to a technique for forming minute biofilms on an anode and a cathode of a microbial battery. Further, the method can be applied to a technique for forming a biofilm for prevention of adhesion of large-sized living organisms to an offshore structure.

In another aspect, the present invention provides a biological waste treatment method including the step of adding one or more of the microbial activity improvement agents described above into sludge of a biological waste treatment facility.

According to this method, it is possible to achieve, at a low cost, improvement in the treatment capacity of biological waste treatment facilities that transcends the limit of improvement in the treatment capacity by a conventional method.

In another aspect, the present invention provides use of a compound selected from the group consisting of compounds represented by the following formulae (1) to (4) or a salt thereof for production of a microbial activity improvement agent:

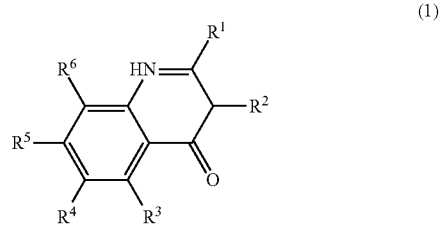

-continued

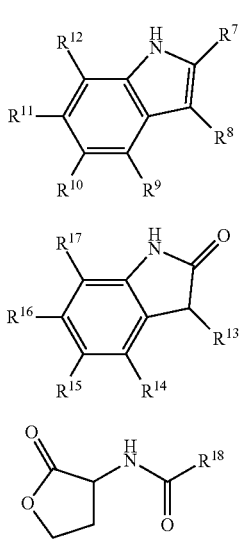

wherein, $R^1$ to $R^6$ each independently represents a hydrogen atom, a hydroxyl group, or a $C_{1-6}$ alkyl group; $R^7$ to $R^{17}$ each independently represent a hydrogen atom or a group represented by any of the following formulae (5) to (7):

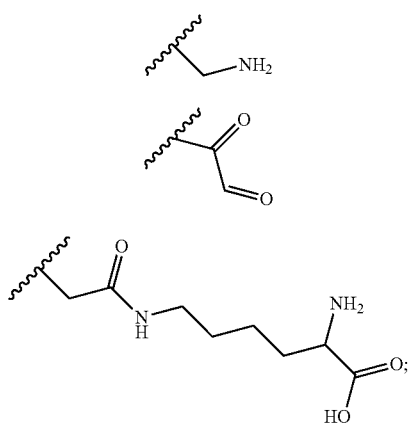

and $R^{18}$ represents a $C_{9-15}$ alkyl group optionally having an oxo group.

In the above use for production of a microbial activity improvement agent, it is more preferable that the compound or the salt thereof be compounds represented by the following formulae (a) to (g):

(a) a compound represented by the above formula (1) wherein $R^1$ to $R^6$ are hydrogen atoms;

(b) a compound represented by the above formula (1) wherein $R^2$ to $R^6$ are hydrogen atoms, and $R^1$ is a methyl group;

(c) a compound represented by the above formula (1) wherein $R^1$ is a methyl group, $R^2$ is a hydroxyl group, and $R^3$ to $R^6$ are hydrogen atoms;

(d) a compound represented by the above formula (2) wherein $R^7$ to $R^{12}$ are hydrogen atoms;

(e) a compound represented by the above formula (2) wherein $R^7$ and $R^9$ to $R^{12}$ are hydrogen atoms, and $R^8$ is a group represented by any of the above formulae (5) to (7);

(f) a compound represented by the above formula (3) wherein $R^{13}$ to $R^{17}$ are hydrogen atoms; and (g) a compound represented by the above formula (4) wherein $R^{18}$ is a $C_{10-15}$ alkyl group or a 2-oxononyl group.

Advantageous Effects of Invention

By adding an extremely small amount of a microbial activity improvement agent of the present invention into a reaction tank of a biological waste treatment facility, it is possible to improve, at a low cost, waste treatment capacity to an extent that is not achievable by a conventional method.

Further, according to a microbial activity improvement method of the present invention, formation of a microbial biofilm is controlled, thereby making it possible to obstruct formation of a biofilm, to foam minute biofilms on an anode and a cathode of a microbial battery, and to form a biofilm on a surface of an offshore structure so as to prevent adhesion of large-sized living organisms.

DESCRIPTION OF EMBODIMENTS

Figure 1:
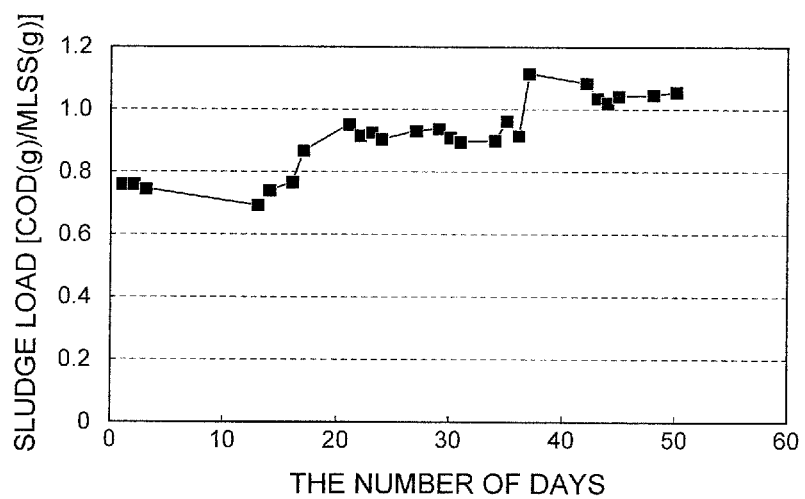
FIG. 1 is a graph showing a transition of sludge load.

As a microbial activity improvement agent of the present invention, a commercial compound can be used. Alternatively, the microbial activity improvement agent of the present invention can be chemically synthesized by a well-known method with the use of commercial compounds as starting materials. The microbial activity improvement agent may be compounds represented by the above formulae (1) to (4) or salts thereof, wherein $R^1$ to $R^6$ each independently represents a hydrogen atom, a hydroxyl group, or a $C_{1-6}$ alkyl group; $R^7$ to $R^{17}$ each independently represent a hydrogen atom or a group represented by any of the above formulae (5) to (7); and $R^{18}$ represents a $C_{9-15}$ alkyl group optionally having an oxo group.

In the group represented by $R^1$ to $R^6$ in the above formula (1), the $C_{1-6}$ alkyl group is preferably a linear alkyl group, and particularly preferably a methyl group. Further, in the group represented by $R^{18}$ in the above formula (4), the $C_{9-15}$ alkyl group optionally having an oxo group is preferably a linear alkyl group, and when the group has an oxo group, it is preferable that the number of oxo groups be 1 and the group have the oxo group at the 2-position.

It is further preferable that the microbial activity improvement agent be compounds represented by the following formulae (8) to (21) or salts thereof.

Examples of the salts include acid addition salts and base addition salts. Examples of the acid addition salts include: halogenated hydroacid salts such as hydrochloride, hydrofluoride, hydrobromate, and hydroiodide; inorganic acid salts such as nitrate, perchlorate, sulfate, phosphate, and carbonate; lower alkylsulfonate salts such as methanesulfonate, trifluoromethanesulfonate, and ethanesulfonate; aryl sulfonates such as benzenesulfonate and p-toluenesulfonate; and organic salts such as fumarate, succinate, citrate, tartrate, oxalate, and maleate. Examples of the base addition salts include: alkali metal salts such as sodium and potassium; alkaline earth metal salts such as calcium and magnesium; and salts with an organic base, such as ammonium salt, guanidine, triethylamine, and dicyclohexylamine.

Alternatively, the microbial activity improvement agent of the present invention can be prepared in such a manner that a specific microorganism is cultured so as to secrete these compounds in a culture medium, and the compounds are extracted from the culture medium. Examples of the microorganism that secretes the above compounds include Gram-negative bacteria such as *Burkholderia, Pseudomonas, Vibrio, Aeromonas, Bacillus, Streptomyces, Streptococcus*, and *Lactobacillus*.

In the present description, the microbial activity refers to activity that a microorganism decomposes specific waste (pollutant). Improvement in the microbial activity refers to that the ability of microorganisms per unit to decompose a specific pollutant is improved. Further, a decrease in the microbial activity refers to that the ability of microorganisms per unit to decompose a specific pollutant decreases. Examples of the pollutant include: sugars such as glucose and maltose; alcohols such as methanol; aldehydes such as formaldehyde; organic solids such as kitchen waste; starch, protein, ammonia, nitrate, dimethylsulfoxide (DMSO), and the like, but the pollutant is not limited to them.

Examples of microorganisms on which the microbial activity improvement agent of the present invention effectively acts include *Vibrio, Aeromonas, Streptomyces, Streptococcus, Lactobacillus, Alcaligenes, Ralstonia, Achromobacter, Halomonas, Burkholderia, Pseudomonas, Rhodobacter, Paracoccus, Sphingobacterium, Flavobacterium, Acidobacterium, Bacillus,* achromobacter, aerobacter, *Brevibacterium, Corynebacterium, Comamonas, Micrococcus, Spirillum, Zoogloea, Clostridium, Dehalococcoides, Aminomonas, Geobacter, Desulfuromonas, Desulfovibrio, Syntrophobacter, Staphylococcus, Methanobacterium, Methanospirillum, Methanosarcina, Methanolinea, Methanobrevibacter*, and *Methanosaeta*.

The concentration of sludge may be represented in terms of MLSS (Mixed liquor suspended solids) in some cases. The measurement of MLSS can be performed by the method described below, for example. At first, a sludge sample is taken into a centrifuge tube, centrifugation is performed at 3,000 rpm for 10 minutes, and then supernatant is removed. Then, water is added to the obtained precipitate and mixed well, centrifugation is performed again and supernatant is removed in the same manner as above. The obtained precipitate is washed and put into an evaporating dish that has been weighted beforehand, and dried in a dryer at 105 to 110° C. for half a day. Subsequently, after standing to cool in a desiccator, the evaporating dish containing the precipitate is weighted. A mass obtained by subtracting a mass of an empty evaporating dish from a measured mass is MLSS.

COD can be measured, for example, by a method as described in JISK0102. More specifically, potassium dichromate and sulfuric acid are added to waste (a sample) to be measured, and a reflux condenser is set to boil the sample for two hours, followed by finding an amount of dichromic acid consumed and representing the amount by an equivalent amount of oxygen. Alternatively, COD may be measured by a method in accordance with a manual of a maker by use of Potable Spectrophotometer (made by HACH Company, model number DR/2400).

A biological waste treatment method of the present invention is achievable by further including, in addition to a conventional biological waste treatment method, the step of adding one or more of the microbial activity improvement agents into a reaction tank of a biological waste treatment facility. The microbial activity improvement agent may be added to waste (wastewater) introduced into the reaction tank of the biological waste treatment facility. The microbial activity improvement agent may be added as a compound chemically synthesized, or extract extracted from culture supernatant obtained as a result of culture of a microorganism of the above specified Gram-negative bacteria may be added. The addition concentration per microbial activity improvement agent ranges preferably from 1 nmol/L to 1 mmol/L, further preferably from 10 nmol/L to 100 µmol/L, and particularly preferably 100 nmol/L to 10 µmol/L, in terms of a final concentration in the reaction tank. The microbial activity improvement agent may be added at a concentration of more than 1 mmol/L, but that may be disadvantageous in terms of cost. Further, even if the microbial activity improvement agent is added at a concentration of less than 1 nmol/L, a sufficient microbial activity-improving effect may not be obtained.

A microbial activity improvement method of the present invention is achievable by including the step of adding, into a cultural environment of a microorganism, the same microbial activity improvement agent as in the biological waste treatment method at a similar concentration.

EXAMPLES

The following shows examples of the present invention to explain the present invention further in details, but the present invention is not limited to these examples and can be altered variously within a scope that does not deviate from the technical idea of the present invention.

Example 1

Preparation of Extract Including Microbial Activity Improvement Agent

Sludges were collected from more than 10 Expanded Granular Sludge Bed (EGSB) plants, and they were acclimated in waste (artificial wastewater) of a composition shown in Table 1. Compositions of a solution A, a solution B, and a solution C in Table 1 are respectively shown in Tables 2 to 4. From these sludges, a sludge having the highest methanogenic activity was selected. Evaluation on the methanogenic activity was carried out by a method described in Example 2. Compounds secreted from a microorganism, included in this sludge, were analyzed by liquid chromatograph time-of-flight mass spectrometry (LC-TOF-MS). As a result, it was demonstrated that compounds represented by the following chemical formulae (8) to (21) existed in this sludge. As a result of estimating the concentrations of the respective compounds from a peak area of the LC-TOF-MS, they were hundreds of nanomoles per liter to tens of micromoles per liter.

TABLE 1

| | |
|---|---|
| Skim milk | 10 g/L |
| $NaHCO_3$ | 4 g/L |
| $K_2HPO_4$ | 4 g/L |
| $NH_4Cl$ | 1 g/L |
| KCl | 1 g/L |
| Solution A | 1 mL/L |
| Solution B | 1 mL/L |
| Solution C | 1 mL/L |

TABLE 2

| Composition of solution A | |
|---|---|
| Urea | 135 g/L |
| $KH_2PO_4$ | 57 g/L |

TABLE 3

| Composition of solution B | |
|---|---|
| $FeSO_4 \cdot 7H_2O$ | 25 g/L |
| $MgSO_4 \cdot 7H_2O$ | 51 g/L |

TABLE 4

| Composition of solution C | |
|---|---|
| $CaCl_2 \cdot 2H_2O$ | 1.0 g/L |
| $ZnCl_2$ | 0.2 g/L |
| $CuCl_2 \cdot 2H_2O$ | 0.1 g/L |
| $MnCl_2 \cdot 4H_2O$ | 0.2 g/L |
| $AlCl_3$ | 0.2 g/L |
| $NiCl_2$ | 0.1 g/L |

After this sludge was put in an ultrasonic cleaner and dispersed by ultrasound at 25° C. for 10 minutes, the sludge was heated at 105° C. for 5 minutes and concentrated by an evaporator, thereby extracting and concentrating the compounds represented by the following chemical formulae (8) to (21), so as to obtain an extract of Example 1.

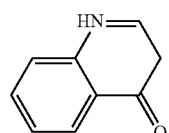
(8)

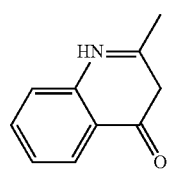
(9)

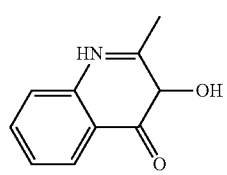
(10)

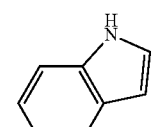
(11)

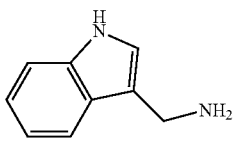
(12)

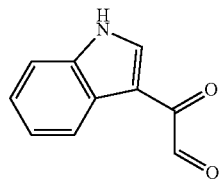
(13)

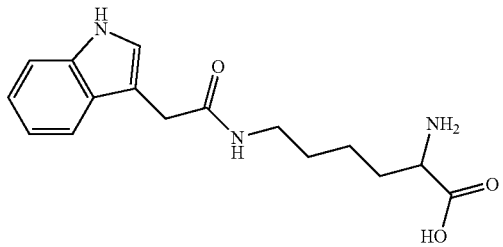
(14)

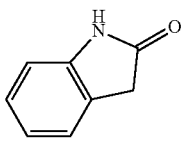
(15)

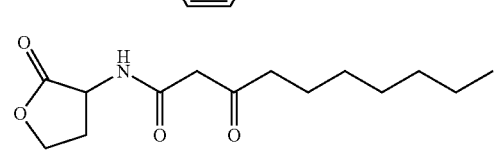
(16)

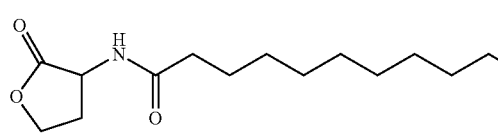
(17)

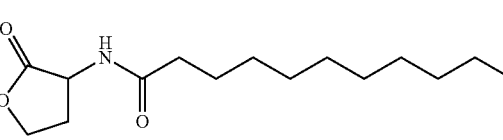
(18)

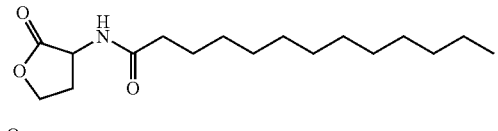
(19)

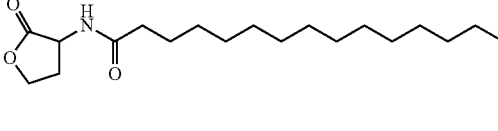
(20)

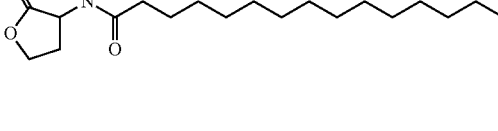
(21)

Example 2

Evaluation on Methanogenic Activity of Sludge

The evaluation on the methanogenic activity of sludge was carried out by determining, by RT-PCR, the quantity of mcrA gene encoding methyl coenzyme M reductase, which is an enzyme peculiar to methanogen. The methanogen is a microorganism that synthesizes methane under anaerobic conditions. It was observed that there was about 10 times difference in the abundance of the mcrA gene between the respective sludge samples. A sludge in which the abundance of the mcrA gene was the highest was selected as a sludge of high methanogenic activity.

Example 3

Evaluation on Microbial Activity Improvement Agent

Sludge was collected from a domestic EGSB plant and broken sludge was removed with a sieve so that granule sludge was prepared. The granule sludge means sludge in which a microorganism is granulated. The diameter of the granule sludge used in the present example was about 1 to 3 mm. Into this granule sludge, artificial waste (artificial wastewater) of COD of 15000 mg/L, which used glucose as a carbon source, was added, and the granule sludge was acclimated for 2 months under a condition of a sludge load of 0.3 [COD (g)/MLSS (g)].

By use of the acclimated granule sludge, biological waste treatment was performed with an Upflow Anaerobic Sludge Blanket (UASB) apparatus. The UASB apparatus used herein was in a cylindrical shape having a capacity of 1.5 L, an inner diameter of 60 mm, and a height of 1 m. Into the UASB apparatus, 500 ml of the granule sludge was put and the waste (artificial wastewater) of a composition shown in Table 5 was supplied, and the biological waste treatment was performed. Compositions of a solution A, a solution B, and a solution C in Table 5 are respectively shown in Tables 2 to 4 above.

TABLE 5

| | |
|---|---|
| Glucose | 15 g/L |
| NH$_4$Cl | 1 g/L |
| NaHCO$_3$ | 4 g/L |
| K$_2$HPO$_4$ | 4 g/L |
| Yeast extract | 0.1 g/L |
| FeSO$_4$•7H$_2$O | 0.3 g/L |
| Solution A | 1 mL/L |
| Solution B | 1 mL/L |
| Solution C | 1 mL/L |

The artificial wastewater used for experiments uses glucose as the only carbon source. Therefore, when a sudden load is applied to the granule sludge, the rate of methane fermentation does not catch up with the rate of acid formation, so that lower fatty acids such as butyrate, propionate, and acetic acid accumulate, thereby resulting in that a reduction in pH is caused and the waste treatment capacity decreases. In the present example, in order to intentionally realize a reduced treatment capacity due to a sudden load, a load that was higher than usual was applied. More specifically, generally, a sludge load of about 0.3 to 0.5 [COD (g)/MLSS (g)] is applied, but in the present experiment, a sludge load of about 0.7 to 1.1 [COD (g)/MLSS (g)] was applied as shown in FIG. 1.

Figure 2:
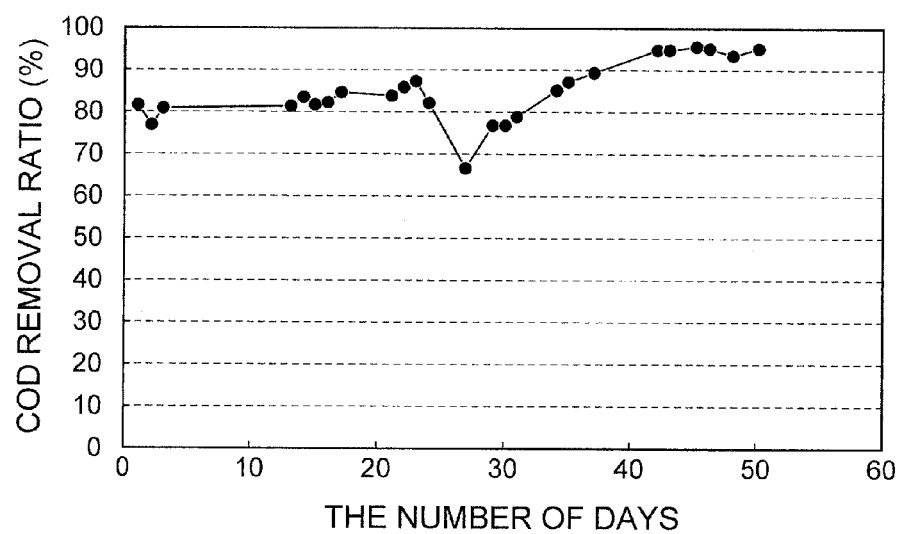
FIG. 2 is a graph showing a transition of COD removal ratio.

As a result, as shown in FIG. 2, a decrease in the treatment capacity was observed on the 27th day from an initiation of the experiment, and the COD removal ratio fell short of 70%. In FIG. 2, the COD removal ratio shows a ratio (%) of a treated pollutant among the applied load (COD). At this point, the concentrations of the lower fatty acids in treated water after the waste treatment in the UASB apparatus were 1300 mg/L for acetic acid and 1800 mg/L for propionate.

At a stage that the waste treatment capacity decreased, the extract of Example 1 was added to the artificial wastewater to be supplied to the UASB apparatus. The addition ratio thereof was 10 mL per 1 L of the artificial wastewater.

As a result of adding the extract of Example 1, remarkable elevation of the microbial activity was observed in about 10 days, and the COD removal ratio reached 90%. After that, even if the sludge load was further increased, the decrease in the microbial activity was not observed, and the COD removal ratio increased to 95%. As shown in FIG. 1, the COD removal ratio before the addition of the extract of Example 1 was about 76 to 88%. Thus, by the addition of the extract of Example 1, the COD removal ratio increased markedly. This result shows that the extract of Example 1 has a remarkable microbial activity-improving effect. The concentrations of the respective compounds represented in the above formulae (8) to (21), which were included in the artificial wastewater, ranged from a few nanomoles per liter to hundreds of nanomoles per liter. Thus, these compounds exhibit a microbial activity-improving effect at a very low concentration. It is what the present inventors found for the first time that in sludge of the biological waste treatment, these compounds are effective for improvement in the waste treatment capacity. Further, in the present example, a waste treatment of 20-50 kg/m$^3$/day was observed, and thus, improvement in the waste treatment capacity was attained.

INDUSTRIAL APPLICABILITY

By adding an extremely small amount of the microbial activity improvement agent of the present invention into a reaction tank of a biological waste treatment facility, it is possible to achieve, at a low cost, improvement in the waste treatment capacity to an extent that is not achievable by a conventional method.

Further, according to the microbial activity improvement method of the present invention, formation of a microbial biofilm is controlled, thereby making it possible to obstruct formation of a biofilm, to form minute biofilms on an anode and a cathode of a microbial battery, and to form a biofilm on a surface of an offshore structure so as to prevent adhesion of large-sized living organisms.

The invention claimed is:
1. A microbial activity improvement method comprising the step of adding one or more compounds selected from the group consisting of compounds represented by the following formulae (1), (3) and (4) or salts thereof into an environment where a microorganism exists:

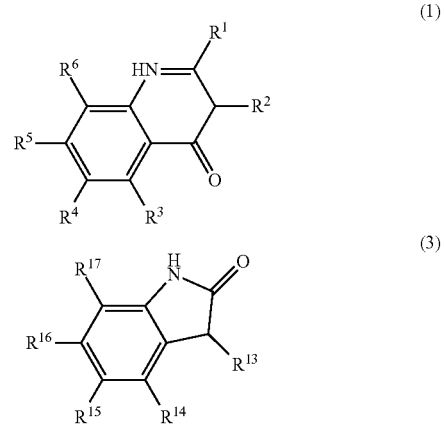

-continued (4)

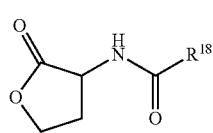

wherein $R^1$ to $R^6$ each independently represents a hydrogen atom, a hydroxyl group, or a $C_{1-6}$ alkyl group; $R^{13}$ to $R^{17}$ each independently represent a hydrogen atom or a group represented by any of the following formulae (5) to (7):

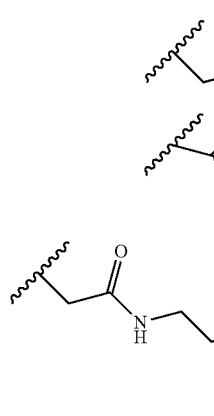

and $R^{18}$ represents a $C_{9-15}$ alkyl group optionally having an oxo group.

2. The microbial activity improvement method according to claim 1, wherein the compounds or the salts thereof are compounds selected from the group consisting of:
(a) a compound represented by the formula (1) wherein $R^1$ to $R^6$ are hydrogen atoms,
(b) a compound represented by the formula (1) wherein $R^2$ to $R^6$ are hydrogen atoms, and $R^1$ is a methyl group,
(c) a compound represented by the formula (1) wherein $R^1$ is a methyl group, $R^2$ is a hydroxyl group, and $R^3$ to $R^6$ are hydrogen atoms,
(d) a compound represented by the formula (3) wherein $R^{13}$ to $R^{17}$ are hydrogen atoms,
(e) a compound represented by the formula (4) wherein $R^{18}$ is a $C_{10-15}$ alkyl group or a 2-oxononyl group, and salts of (a) to (e).

3. A biological waste treatment method comprising the step of adding one or more compounds selected from the group consisting of compounds represented by the following formulae (1), (3) and (4) or salts thereof into a reaction tank of a biological waste treatment facility:

(1)

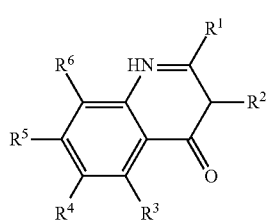

-continued (3)

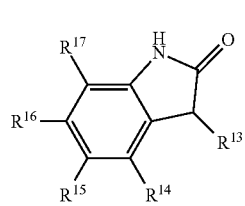

(4)

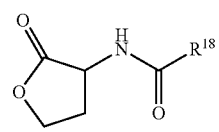

wherein $R^1$ to $R^6$ each independently represents a hydrogen atom, a hydroxyl group, or a $C_{1-6}$ alkyl group; $R^{13}$ to $R^{17}$ each independently represent a hydrogen atom or a group represented by any of the following formulae (5) to (7):

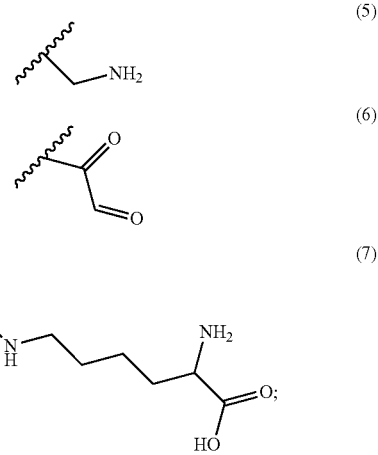

and $R^{18}$ represents a $C_{9-15}$ alkyl group optionally having an oxo group.

4. The biological waste treatment method according to claim 3, wherein the compounds or the salts thereof are compounds selected from the group consisting of
(a) a compound represented by the formula (1) wherein $R^1$ to $R^6$ are hydrogen atoms,
(b) a compound represented by the formula (1) wherein $R^2$ to $R^6$ are hydrogen atoms, and $R^1$ is a methyl group,
(c) a compound represented by the formula (1) wherein $R^1$ is a methyl group, $R^2$ is a hydroxyl group, and $R^3$ to $R^6$ are hydrogen atoms,
(d) a compound represented by the formula (3) wherein $R^{13}$ to $R^{17}$ are hydrogen atoms,
(e) a compound represented by the formula (4) wherein $R^{18}$ is a $C_{10-15}$ alkyl group or a 2-oxononyl group, and salts of (a)-(e).

* * * * *